(12) United States Patent
Magers et al.

(10) Patent No.: US 6,660,028 B2
(45) Date of Patent: *Dec. 9, 2003

(54) METHOD FOR DETERMINING THE EFFECTIVE THERMAL MASS OF A BODY OR ORGAN USING A COOLING CATHETER

(75) Inventors: Michael Magers, Encinitas, CA (US); Steven A. Yon, San Diego, CA (US)

(73) Assignee: Innercool Therapies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/082,964

(22) Filed: Feb. 25, 2002

(65) Prior Publication Data

US 2002/0082671 A1 Jun. 27, 2002

Related U.S. Application Data

(63) Continuation of application No. 09/586,000, filed on Jun. 2, 2000, now Pat. No. 6,383,210.

(51) Int. Cl.[7] .................................................. A61F 7/00

(52) U.S. Cl. ........................................ 607/105; 607/106

(58) Field of Search .......................... 607/96, 104, 105, 607/106, 113; 606/20–23, 27–28

(56) References Cited

U.S. PATENT DOCUMENTS

| | | | |
|---|---|---|---|
| 2,308,484 A | 1/1943 | Auzin et al. | |
| 2,374,609 A | 4/1945 | McCollum | |
| 2,615,686 A | 10/1952 | Davidson | |
| 2,672,032 A | 3/1954 | Towse | |
| 2,913,009 A | 11/1959 | Kuthe | |
| 3,125,096 A | 3/1964 | Antiles et al. | |

(List continued on next page.)

FOREIGN PATENT DOCUMENTS

| | | |
|---|---|---|
| AU | 685559 B2 | 1/1998 |
| AU | 730835 B2 | 3/2001 |
| AU | 734506 B2 | 6/2001 |
| AU | 739996 B2 | 10/2001 |

(List continued on next page.)

OTHER PUBLICATIONS

Grigore, Alina, et al.; *Temperature Regulation and Manipulation During Surgery and Anesthesia;* Anesthesiology Online Journal; 15 pages; available at http://www.aneesthesiologyonline.com/articles/onepage.cfm?chapter_id=11&journal=1 (Released May 1998).

Fulbrook, Paul; *Core Body Temperature Measurement: a Comparison of Axilla, Tympanic Membrane and Pulmonary Artery Blood Temperature;* Intensive and Critical Care Nursing; vol. 13; pp. 266–272 (1997).

Matsukawa, T., et al., ed al.; *Comparison of Distal Oesophageal Temperature with Deep and Tracheal Temperatures;* Canadian Journal of Anaesthesia; vol. 44; No. 4; pp. 433–438 (1997).

(List continued on next page.)

*Primary Examiner*—Roy D. Gibson
(74) *Attorney, Agent, or Firm*—Mayer Fortkort & Williams, PC; Stuart H. Mayer, Esq.

(57) ABSTRACT

A method and apparatus is provided for determining an effective thermal mass of a patient. The effective thermal mass is employed to determine a gain factor used in a feedback control system controlling patient temperature. The method begins by inducing hypothermia or hyperthermia in at least a selected portion of the patient with a device having a heat transfer surface. Next, power is transferred between the device and the patient. A change in temperature over time, which arises in the selected portion of the patient, is measured while performing the step of inducing hypothermia or hyperthermia. Finally, an effective thermal mass is calculated based on the measured power and the measured temperature change over time.

29 Claims, 2 Drawing Sheets

U.S. PATENT DOCUMENTS

| | | |
|---|---|---|
| 3,298,371 A | 1/1967 | Lee |
| 3,370,153 A | 2/1968 | Du Fresne et al. |
| 3,413,438 A | 11/1968 | Gardner et al. |
| 3,425,419 A | 2/1969 | Dato |
| 3,504,674 A | 4/1970 | Swenson et al. |
| 3,612,175 A | 10/1971 | Ford et al. |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,127,365 A | 11/1978 | Martin et al. |
| 4,153,048 A | 5/1979 | Magrini |
| 4,165,206 A | 8/1979 | Martin et al. |
| 4,190,033 A | 2/1980 | Foti |
| 4,231,425 A | 11/1980 | Engstrom |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,375,941 A | 3/1983 | Child |
| 4,427,009 A | 1/1984 | Wells et al. |
| 4,445,500 A | 5/1984 | Osterholm |
| 4,483,341 A | 11/1984 | Witteles |
| 4,493,625 A | 1/1985 | Pieters |
| 4,502,286 A | 3/1985 | Okada et al. |
| 4,532,414 A | 7/1985 | Shah et al. |
| 4,569,355 A | 2/1986 | Bitterly |
| 4,581,017 A | 4/1986 | Sahota |
| 4,585,056 A | 4/1986 | Oscarsson |
| 4,593,258 A | 6/1986 | Block |
| 4,602,642 A | 7/1986 | O'Hara et al. |
| 4,638,436 A | 1/1987 | Badger et al. |
| 4,655,746 A | 4/1987 | Daniels et al. |
| 4,672,962 A | 6/1987 | Hershenson |
| 4,707,587 A | 11/1987 | Greenblatt |
| 4,731,072 A | 3/1988 | Aid |
| 4,739,492 A | 4/1988 | Cochran |
| 4,745,922 A | 5/1988 | Taylor |
| 4,745,928 A | 5/1988 | Webler et al. |
| 4,747,826 A | 5/1988 | Sassano |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,033 A | 11/1988 | Steyert et al. |
| 4,781,799 A | 11/1988 | Herbert, Jr. et al. |
| 4,789,000 A | 12/1988 | Aslanian |
| 4,796,640 A | 1/1989 | Webler |
| 4,819,655 A | 4/1989 | Webler |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,917,687 A | 4/1990 | O'Boyle |
| 4,920,963 A | 5/1990 | Brader |
| 4,951,677 A | 8/1990 | Crowley et al. |
| 4,964,409 A | 10/1990 | Tremulis |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishiwara et al. |
| 5,106,368 A | 4/1992 | Uldall et al. |
| 5,108,390 A | 4/1992 | Potocky et al. |
| RE33,911 E | 5/1992 | Samson et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,174,285 A | 12/1992 | Fontenot |
| 5,180,364 A | 1/1993 | Ginsburg |
| 5,180,896 A | 1/1993 | Gibby et al. |
| 5,190,539 A | 3/1993 | Fletcher et al. |
| 5,191,883 A | 3/1993 | Lennox et al. |
| 5,196,024 A | 3/1993 | Barath |
| 5,197,466 A | 3/1993 | Marchosky et al. |
| 5,211,631 A | 5/1993 | Sheaff |
| 5,226,286 A | 7/1993 | Mo |
| 5,234,405 A | 8/1993 | Klatz et al. |
| 5,234,413 A | 8/1993 | Wonder et al. |
| 5,241,951 A | 9/1993 | Mason et al. |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,284,423 A | 2/1994 | Holdsworth et al. |
| 5,306,261 A | 4/1994 | Alliger et al. |
| 5,310,440 A | 5/1994 | Zingher |
| D347,890 S | 6/1994 | Eads |
| D348,101 S | 6/1994 | Poli et al. |
| 5,320,503 A | 6/1994 | Davis |
| 5,322,514 A | 6/1994 | Steube et al. |
| 5,322,515 A | 6/1994 | Karas et al. |
| 5,322,518 A | 6/1994 | Schneider et al. |
| 5,324,319 A | 6/1994 | Mason et al. |
| 5,326,165 A | 7/1994 | Walthall et al. |
| 5,326,166 A | 7/1994 | Walthall et al. |
| 5,326,236 A | 7/1994 | Kramer et al. |
| 5,328,461 A | 7/1994 | Utterberg |
| 5,330,435 A | 7/1994 | Vaillancourt |
| 5,330,438 A | 7/1994 | Gollobin et al. |
| 5,330,519 A | 7/1994 | Mason et al. |
| 5,331,309 A | 7/1994 | Sakai |
| 5,332,399 A | 7/1994 | Grabenkort et al. |
| 5,334,179 A | 8/1994 | Poli et al. |
| 5,334,180 A | 8/1994 | Adolf et al. |
| 5,334,182 A | 8/1994 | Simons et al. |
| 5,334,188 A | 8/1994 | Inoue et al. |
| 5,334,193 A | 8/1994 | Nardella |
| 5,334,197 A | 8/1994 | Kriesel et al. |
| 5,336,190 A | 8/1994 | Moss et al. |
| 5,339,511 A | 8/1994 | Bell |
| 5,340,290 A | 8/1994 | Clemens |
| 5,342,181 A | 8/1994 | Schock et al. |
| 5,342,182 A | 8/1994 | Montoya et al. |
| 5,342,301 A | 8/1994 | Saab |
| 5,342,346 A | 8/1994 | Honda et al. |
| 5,342,347 A | 8/1994 | Kikuchi et al. |
| 5,343,734 A | 9/1994 | Maeda et al. |
| 5,344,436 A | 9/1994 | Fontenot et al. |
| 5,346,466 A | 9/1994 | Yerlikaya et al. |
| 5,352,213 A | 10/1994 | Woodard |
| 5,354,186 A | 10/1994 | Murtuza et al. |
| 5,354,264 A | 10/1994 | Bae et al. |

| Patent No. | Date | Inventor |
|---|---|---|
| 5,354,272 A | 10/1994 | Swendson et al. |
| 5,364,364 A | 11/1994 | Kasvikis et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,391,142 A | 2/1995 | Sites et al. |
| 5,395,311 A | 3/1995 | O'Neil et al. |
| 5,395,314 A | 3/1995 | Klatz et al. |
| 5,395,331 A | 3/1995 | O'Neill et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,664 A | 8/1995 | Cohen et al. |
| 5,437,673 A | 8/1995 | Baust et al. |
| 5,443,456 A | 8/1995 | Alliger et al. |
| 5,462,521 A | 10/1995 | Brucker et al. |
| 5,466,131 A | 11/1995 | Altham et al. |
| 5,486,204 A | 1/1996 | Clifton |
| 5,486,208 A | 1/1996 | Ginsburg |
| 5,496,271 A | 3/1996 | Burton et al. |
| 5,514,094 A | 5/1996 | Anello et al. |
| 5,529,067 A | 6/1996 | Larsen et al. |
| 5,531,776 A | 7/1996 | Ward et al. |
| 5,549,559 A | 8/1996 | Eshel |
| 5,558,644 A | 9/1996 | Boyd et al. |
| 5,573,532 A | 11/1996 | Chang |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,702,234 A | 12/1997 | Pieters |
| 5,702,358 A | 12/1997 | Witherspoon et al. |
| 5,709,654 A | 1/1998 | Klatz et al. |
| 5,713,941 A | 2/1998 | Robins et al. |
| 5,716,386 A | 2/1998 | Ward et al. |
| 5,730,720 A | 3/1998 | Sites et al. |
| 5,733,318 A | 3/1998 | Augustine |
| 5,733,319 A | 3/1998 | Neilson et al. |
| 5,735,809 A | 4/1998 | Gorsuch |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,837,003 A | 11/1998 | Ginsburg |
| 5,861,021 A | 1/1999 | Thome et al. |
| 5,868,735 A | 2/1999 | Lafontaine |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,893,885 A | 4/1999 | Webster, Jr. |
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,918,981 A | 7/1999 | Ribi |
| 5,957,917 A | 9/1999 | Doiron et al. |
| 5,957,963 A | 9/1999 | Dobak, III |
| 5,964,751 A | 10/1999 | Amplatz et al. |
| 5,968,009 A | 10/1999 | Siman |
| 5,971,979 A | 10/1999 | Joye et al. |
| 5,989,238 A | 11/1999 | Ginsburg |
| 6,007,692 A | 12/1999 | Herbert et al. |
| 6,019,783 A | 2/2000 | Philips et al. |
| 6,022,336 A | 2/2000 | Zadno-Azizi |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,063,101 A | 5/2000 | Jacobsen et al. |
| 6,096,068 A | 8/2000 | Dobak, III et al. |
| 6,110,168 A | 8/2000 | Ginsburg |
| 6,113,593 A | 9/2000 | Tu et al. |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,194,899 B1 | 2/2001 | Ishihara et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,264,680 B1 | 7/2001 | Ash |
| 6,287,326 B1 | 9/2001 | Pecor |
| 6,290,696 B1 | 9/2001 | Lafontaine |
| 6,290,697 B1 | 9/2001 | Tu et al. |
| 6,290,717 B1 | 9/2001 | Philips |
| 6,295,990 B1 | 10/2001 | Lewis et al. |
| 6,299,599 B1 | 10/2001 | Pham et al. |
| 6,303,156 B1 | 10/2001 | Ferrigno |
| 6,306,161 B1 | 10/2001 | Ginsburg |
| 6,312,452 B1 | 11/2001 | Dobak, III et al. |
| 6,315,995 B1 | 11/2001 | Pinsky et al. |
| 6,316,403 B1 | 11/2001 | Pinsky et al. |
| 6,325,818 B1 | 12/2001 | Werneth |
| 6,336,911 B1 | 1/2002 | Westerbeck |
| 6,338,727 B1 | 1/2002 | Noda et al. |
| 6,364,899 B1 | 4/2002 | Dobak, III |
| 6,368,304 B1 | 4/2002 | Aliberto et al. |
| 6,379,378 B1 | 4/2002 | Werneth et al. |
| 6,383,210 B1 | 5/2002 | Magers et al. |
| 6,393,320 B2 | 5/2002 | Lasersohn et al. |
| 6,451,011 B2 | 9/2002 | Tu |
| 6,458,150 B1 | 10/2002 | Evans et al. |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |

| | | | |
|---|---|---|---|
| 2001/0002442 A1 | 5/2001 | Dobak, III | |
| 2001/0005791 A1 | 6/2001 | Ginsburg et al. | |
| 2001/0007940 A1 | 7/2001 | Tu et al. | |
| 2001/0007951 A1 | 7/2001 | Dobak, III | |
| 2001/0008975 A1 | 7/2001 | Dobak, III et al. | |
| 2001/0009610 A1 | 7/2001 | Augustine et al. | |
| 2001/0010011 A1 | 7/2001 | Aliberto et al. | |
| 2001/0011184 A1 | 8/2001 | Dobak, III et al. | |
| 2001/0011185 A1 | 8/2001 | Dobak, III et al. | |
| 2001/0014802 A1 | 8/2001 | Tu | |
| 2001/0016763 A1 | 8/2001 | Lasheras et al. | |
| 2001/0016764 A1 | 8/2001 | Dobak, III | |
| 2001/0021865 A1 | 9/2001 | Dobak, III et al. | |
| 2001/0021866 A1 | 9/2001 | Dobak, III et al. | |
| 2001/0029394 A1 | 10/2001 | Dobak, III et al. | |
| 2001/0031946 A1 | 10/2001 | Walker et al. | |
| 2001/0032003 A1 | 10/2001 | Pecor | |
| 2001/0032004 A1 | 10/2001 | Werneth | |
| 2001/0039440 A1 | 11/2001 | Lasheras et al. | |
| 2001/0041923 A1 | 11/2001 | Dobak, III | |
| 2001/0044644 A1 | 11/2001 | Keller et al. | |
| 2001/0047191 A1 | 11/2001 | Lasersohn et al. | |
| 2001/0047192 A1 | 11/2001 | Lasersohn et al. | |
| 2001/0047196 A1 | 11/2001 | Ginsburg et al. | |
| 2001/0049545 A1 | 12/2001 | Lasersohn et al. | |
| 2002/0002394 A1 | 1/2002 | Dobak, III | |
| 2002/0004675 A1 | 1/2002 | Lasheras | |
| 2002/0007179 A1 | 1/2002 | Dobak, III et al. | |
| 2002/0007202 A1 | 1/2002 | Dobak, III et al. | |
| 2002/0007203 A1 | 1/2002 | Gilmartin et al. | |
| 2002/0016621 A1 | 2/2002 | Werneth et al. | |
| 2002/0022823 A1 | 2/2002 | Worthen et al. | |
| 2002/0026227 A1 | 2/2002 | Phillips | |
| 2002/0029016 A1 | 3/2002 | Pham et al. | |
| 2002/0032430 A1 | 3/2002 | Luo et al. | |
| 2002/0032474 A1 | 3/2002 | Dobak, III et al. | |
| 2002/0040717 A1 | 4/2002 | Dobak, III | |
| 2002/0045852 A1 | 4/2002 | Saab | |
| 2002/0045892 A1 | 4/2002 | Kramer | |
| 2002/0045925 A1 | 4/2002 | Keller et al. | |
| 2002/0049409 A1 | 4/2002 | Noda et al. | |
| 2002/0049410 A1 | 4/2002 | Noda et al. | |
| 2002/0049484 A1 | 4/2002 | Werneth et al. | |
| 2002/0082671 A1 | 6/2002 | Magers | |
| 2002/0111584 A1 | 8/2002 | Walker et al. | |
| 2002/0111657 A1 | 8/2002 | Dae et al. | |
| 2003/0023288 A1 | 1/2003 | Magers | |

FOREIGN PATENT DOCUMENTS

| | | |
|---|---|---|
| CA | 2177982 | 6/1995 |
| CN | 1082382 A | 2/1994 |
| EP | 0 655 225 A1 | 5/1993 |
| EP | 0 664 990 | 11/1997 |
| EP | 0 428 505 B2 | 3/2001 |
| EP | 1205167 A2 | 5/2002 |
| EP | 1029520 B1 | 8/2002 |
| FR | 2447406 | 3/1980 |
| SU | 806 029 | 2/1981 |
| WO | WO 91/05528 | 3/1993 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 98/26831 | 6/1998 |
| WO | WO 98/31312 | 7/1998 |
| WO | WO 99/04211 | 1/1999 |
| WO | WO 99/05996 | 2/1999 |
| WO | WO 99/37226 | 7/1999 |
| WO | WO 99/48449 | 9/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/53246 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 5/2001 |
| WO | WO 01/87379 | 5/2001 |
| WO | WO 01/95840 | 5/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 01/87174 | 11/2001 |
| WO | WO 02/07793 | 1/2002 |
| WO | WO 02/19934 | 3/2002 |
| WO | WO 02/26175 | 4/2002 |
| WO | WO 02/26176 | 4/2002 |
| WO | WO 02/26285 | 4/2002 |
| WO | WO 02/26307 | 4/2002 |
| WO | WO 02/28300 | 4/2002 |
| WO | WO 02/36180 | 5/2002 |
| WO | WO 02/38091 | 5/2002 |

OTHER PUBLICATIONS

Benzinger, Maria; *Tympanic Thermometry in Surgery and Anesthesia;* JAMA; vol. 209, No. 8; pp. 1207–1211 (Aug. 25, 1969).

Kinney, Thomas B., et al.; *Optimizing Myocardial Hypothermia: I. Temperature Probe Design and Clinical Inferences;* Ann. Thorac. Surg.; vol. 51; pp. 278–283 (1991).

Hills, Gordon A., et al.; *Apparatus for Controlling Temperature of Catheter Contents in Cold Environments (T–Control, 2);* Laboratory Animal Science; vol. 27, No. 6; pp. 1028–1030 (Dec. 1977).

Author Unknown; *Gorman–Rupp Hypothermia Machine;* Health Devices; pp. 190–191 (Apr. 1972).

Author Unknown; *Gorman–Rupp Hypothermia Machine (T–Control, 3);* Health Devices; pp. 263–265 (Jul.–Aug., 1972).

Baumann, Carol K., et al; *Volumetric Interstitial Hyperthermia;* Aorn Journal; vol. 50; No. 2; pp. 258–274 (Aug. 1989).

Margin, R.L., et al.; *Local Tumor Hyperthermia Using a Computer–controlled Microwave System;* Bioelectromagnetics, vol. 3; pp. 363–370 (1982).

Sapareto, S.A.; *Biology of Hyperthemia in Vito* ; In Physical Aspects of Hyperthermia. Nussbaum G. (Ed.), American Institute of Physics Inc., pp. 1–19.

Ambrus, "The Biphasic Nature and Temperature Dependence of the Activation of Human Plasminogen by Urokinase," Research Communications in Chemical Pathology and Pharmacology, vol. 24, No. 2, May, 1979, pp. 339–347.

Bigelo, "Hypothermia, Its Possible Role in Cardiac Surgery," Annals of Surgery, vol. 132, No. 5, Nov., 1959, pp. 849–866.

Cheatle, "Cryostripping the Long and Short Saphenous Veins," Br. J. Surg., vol. 80, Jan. 1993.

Dexter, "Blood Warms as it Blows Retrograde from a Femoral Cannulation Site to the Carotid Artery During Cardiopulmonary Bypass," Perfusion, vol. 9, No. 6, Nov. 1994, pp. 393–397.

Dr. Gravenstein, *Temperaure, Clinical Monitoring Practices,* pp. 208–210.

Elenor R. Adair, *Thermoregulation In the Presence of Microwave Fields, Handbook of Biological Effects of Electromagnetic Fields,* Chapter 10, pp. 403–433.

Gillinov, "Superior Cerebral Protection with Profound Hypothermia During Circulatory Arrest," Ann. Thorac. Surg., vol. 55, No. 1992, pp. 1432–1439.

Higazi, "The Effect of Ultrasonic Irradiation and Temperature on Fibrinolytic Activity in Vitro," Thrombosis Research, vol. 69, No. 2, Aug. 1992, pp. 251–253.

Imamaki, "Retrograde Cerebral Perfusion with Hypothermic Blood Provides Efficient Protection of the Brain," Journal of Cardiac Surgery, vol. 10, No. 4, Part 1, Jul. 1995, pp. 325–333.

Jolin, "Management of a Giant Intracranial Aneurysm Using Surface–Heparinized Extracorporeal Circulation and Controlled Deep Hypothermic Low Flow Perfusion," Acta Anaesthesiologica Scandinavia, Aug. 1992, pp. 756–760.

Joseph R.C. Jansen, PhD et al., "Near Continuous Cardiac Output by Thermodilution," Journal of Clinical Monitoring, vol. 13:233–239.

Kimoto, "Open Heart Surgery Under Direct Vision with the Aid of Brain–Cooling by Irrigation," Surgery, vol. 39, No. 4, Jul. 1955, pp. 592–603.

Marekovic, Z., Abstract of "Renal Hypotermia in Situ by Veneous Passages: Experimental Work on Dogs," Eur Urol 6(2), 1980, 1 page.

Meden, "Effect of Hypothermia and Delayed Thrombolysis in a Rat Embolic Stroke Model," Acta Neurologica Scandinavica, Dec. 1993, pp. 91–98.

Meden, "The Influence of Body Temperature on Infarct Volume and Thromolytic Therapy in a Rat embolic Stroke Model," Brain Research, vol. 647, Feb. 1994, pp. 131–138.

Milleret, Rene, "La cryo–chirugie danes les varices des mimbres inferieurs," Angiologie, Supplement No. 110.

Milleret, Abstract of "Cryosclerosis of the Saphenous Veins in Varicose Reflux in the Obese and Elderly," Phlebologie, vol. 34, No. 4, Oct. 1981, one page.

Parkins, "Brain cooling in the Prevention of brain Damage During Periods of Circulatory Occlusion in Dogs," Annals of Surgery, vol. 140, No. 3, Apr. 1954, pp. 284–289.

Piepgras, "Rapid Active Internal Core Cooling for Induction of Moderate Hypothermia in Head Injury by Use of an Extracroporeal Heat Exchanger," Neurosurgery, vol. 42, No. 2, Feb. 1998, pp. 311–318.

Rijken, "Plasminogen Activation at Low Temperatures in Plasma Samples Containing Therapeutic Concentrations of Tissue–Type Plasminogen Activator of Other Thrombolytic Agents," Place of Publication Unknown, Oct. 1989, pp. 47–52.

Schwartz, A.E. et al., "Isolated cerebral hypothermia by single carotid artery perfusion of extracorporeally cooled blood in baboons," Neurosurgery 39(3): 577–582.

Schwartz, "Cerebral Blood Flow During Low–Flow Hypothermic Cardiopulmonary Bypass in Baboons," Anesthesiology, vol. 81, No. 4, Jun. 1994, pp. 959–964.

Schwartz, "Selective Cerebral Hypothermia by Means of Transfemoral Intenral Carotid Artery Catheterization," Radiology, vol. 201, No. 2, May 1996, pp. 571–572.

Sessler, "Temperature–Monitoring and Thermal Management Guidelines," Anesthesiology 1998; 89:1298–1300.

Shiraki, K. et al., "Esophageal and Tympanic Temperature Responses to Core Blood Temperature Changes During Hyperthermia," The American Physiological Society, 1986, pp. 98–102.

Steen, "The Detrimental Effects of Prolonged Hypothermia and Rewarming in the Dog," Anesthesiology, vol. 52, No. 3, Aug. 1979. pp. 224–230.

Vandam, "Hypothermia", The New England Journal of Medicine, Sep. 1959, pp. 546–553.

White, "Cerebral Hypothermia and Circulatory Arrest," Mayo Clinic Proceedings, vol. 53, Jul. 1978, pp. 450–458.

Yenari, "Thrombolysis with Tissue Plasminogen Activator (TPA) is Temperature Dependent," Thrombosis Research, vol. 77, No. 5, Jul. 1994, pp. 475–481.

Yoshihara, "Changes in Coagulation and Fibrinolysis Occurring in Dogs During Hypothermia," Thrombosis Research, vol. 37, No. 4 Aug. 1984, pp. 503–512.

Zarins, "Circulation in Profound Hypothermia," Journal of Surgical Research, vol. 14, No. 2, Nov. 1972, pp. 97–104.

Acton, J.C., L. C. Sheppard, N.T. Kouchoukos, J.W. Kirklin, *Automated Care Systems, for Critically III Patients Following Cardiac Surgery,* Dept. of Surgery, University of Alabama in Birmingham, Birmingham, Alabama 35294, pp. 111–115.

Anon, *Automatic Feedback Instrumentation for Hospital Room Utilizing Microsensors,* IBM Technical 'Disclosure Bulletin, Aug., 1986, vol. 29 (3): 1320.

Benzinger, T.H. "On Physical Heat Regulation and Sense of Temperature in Man" 1959.

Carrol, D.L., C. Finn, S. Gill, J. Sawyer, and B. Judge, *A Comparison of Measurements from a temporal Artery of Thermometer and a Pulmonary Arter Thermistor—Preliminary Results.*

Colvett, K. T. et al. *Opportunities with Combined Modality Therapy for Selective Orogan Preservation in Muscle–Invasive Bladder Cancer,* J. Surg. Oncology 1996; 63:201–208.

DeFord, et al., *Design and Evaluation of Closed–Loop Feedback Control of Minimum Temperatures in Human Intracranial Tumours Treated with Interstitial Hyperthermia,* Med. & Biol. Eng. & Comput. 1991, 29:197–206.

Frank et al. "Relative contribution of core and cutaneous temperatures to thermal comfort and autonomic responses in humans." 1999.

Frank et al. "Age–related thermoregulatory differences during core cooling in humans." 2000.

Gentilello, L.M. "Advances in Management of Hypothermia" 1995.

Gerbrandy et al. "Oral, Rectal, and esophageal temperatures in relation to central temperature control man." 1954.

Goldstein and Frank, "the wisdom of the body revisited: the adrenomedullary response to mild core hypothermia in humans." Endocrine Regulations vol. 35, 3–7, 2001.

Haley et al. "A Randomized Tirilazad Mesylate in Patients with Acute Stroke (RANTTAS). The RANTTAS Investigators" Stroke 27(9)1996.

Hayes, et al. *Temperature Control in Extracororeal Circulation,* New Appliances, Aug. 17, 1988, p. 430.

Jessen et al. "Intravascular heat Exchanger for Conscious Goats." Pflögers Archive 368, 263–265, 1977.

Kogaku, I.T.S. "Sensor technology to control artificial organs" lyodenshi To Seita Kogaku 22:4, Aug. 1984.

Maas, C. et al., *Intermittent Antegrade/Selective Cerebral Perfusion during Circulatory Arrest for Repair o the Aortic Arch,* Perfusion 1997; 12:127–132.

Mercer and Jessen "Effects of Total Body Core Cooling on Heat Production of Conscious Goats" Pflügers Archive 373, 259–267, 1978.

Moller, P.H. et al. "Temperature control and light penetration in a feedback interstitial laser thermotherapy system" Int. J. Hyperthermia vol. 2, Jan. 1996.

Olshausen et al. *An Isothermal Flowmeter with Improved Frequency Response for Measuring Tissue Blood Flow,* 1976, Pflügers Arch., 2367:97–102.

METHOD FOR DETERMINING THE EFFECTIVE THERMAL MASS OF A BODY OR ORGAN USING A COOLING CATHETER

CROSS-REFERENCE TO RELATED APPLICATION

This Application is a continuation of co-pending U.S. patent application Ser. No. 09/586,000, filed Jun. 2, 2000 entitled "Method for Determining the Effective Thermal Mass of a Body or Organ Using a Cooling Catheter" now U.S. Pat. No. 6383,210B1.

BACKGROUND OF THE INVENTION

I. Field of the Invention

The present invention relates generally to the modification and control of the temperature of the whole body or a selected body organ. More particularly, the invention relates to a method for controlling whole body or organ temperature by selecting an appropriate gain based on the mass of the body or organ.

II. Description of the Related Art

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Catheters have been developed which are inserted into the bloodstream of the patient in order to induce total body hypothermia. For example, U.S. Pat. No. 3,425,419 to Dato describes a method and apparatus of lowering and raising the temperature of the human body. The Dato invention is directed towards a method of inducing moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. However, use of the Dato invention implicates certain negative effects of total body hypothermia.

Due to certain problems associated with total body hypothermia, attempts have been made to provide more selective cooling by intravascularly regulating the temperature of a selected organ. For example, a heat transfer element such as disclosed in Appl. Ser. No. 09/103,342 may be placed in the feeding artery of the organ to absorb or deliver the heat from or to the blood flowing into the organ. The transfer of heat may cause either a cooling or a heating of the selected organ. The heat transfer element is small enough to fit within the feeding artery while still allowing a sufficient blood flow to reach the organ in order to avoid ischemic organ damage. By placing the heat transfer element within the feeding artery of an organ, the temperature of an organ can be controlled without significantly affecting the remaining parts of the body.

The human thermoregulatory system usually maintains a core body temperature near 37° C. but during induced anesthesia, the patient's thermoregulatory defense mechanisms are inhibited. This inhibition lowers the patient's threshold for vasoconstriction and shivering so that the patient losses the ability to control his or her core temperature. In this state of anesthesia, hypothermia can arise from environmental factors, the exposure of body cavities, and the use of active cooling devices. As a result, anesthetized patients are poikilothermic, with body temperatures determined by the environment, over about a 4° C. range of core temperatures.

External cooling/rewarming devices are currently used in surgical procedures to induce hypothermia or to return to normothermic conditions after hypothermia. These devices transport heat flux through the skin, which is an ineffective way to achieve heat transfer because as a result of the different vasoconstrictive states of the patient, blood may not be communicating from the core to the periphery. Endovascular core cooling/rewarming techniques can be much more effective in altering the temperature state of the patient. However, with enhanced effectiveness comes the need to control the degree of heat transfer that is provided to induce, control, and maintain the desired thermal state. Ideally, a heat balance can be achieved by a closed loop feedback system in which the patient's core temperature is sensed and continuously monitored with a standard disposable temperature probe. The temperature is fed back to a controller, which alters the rate of heat transfer through the endovascular catheter, thus achieving the desired temperature state of the patient.

Various feedback control algorithms can be used to control the rate at which heat is extracted from or delivered to the body. In this way the temperature of the body or organ can be varied at a controlled rate and/or maintained at a desired temperature. These algorithms determine the flow rate or temperature of the fluid that is circulated through the catheter based on the temperature history and instantaneous differential between the patient's desired temperature and the patients' actual temperature. The gain of the feedback control system is defined in terms of the power extracted or delivered by the catheter per unit temperature differential between the patient's desired and actual temperature, which is also known as the servo error.

A common feedback control algorithm is incorporated in a PID (proportional-integral-derivative) controller. The parameters used by a PID controller include a gain factor, an integral factor, and a derivative factor to adjust the power transferred by the catheter to control the patients' temperature. An optimal feedback control algorithm should precisely control the patient's temperature by minimizing the system's error in response to a command, i.e. a desired temperature state. Depending on the patients' thermal environment, level of anesthesia, and the surgical manipulations performed on the patient, thermal disturbances are created. The task of the feedback control system is to add or subtract heat from the patient to balance out these thermal disturbances to achieve a neutral heat balance between the patient and his or her environment.

It is important that a proper feedback control gain factor be employed when cooling (or heating) a given body or organ. For example, if the selected gain is too high, the body's response to such a relatively rapid rate of cooling will be to overshoot the target temperature, which may induce a series of damped temperature oscillations about the target temperature. If the gain factor chosen is optimal, the body's response to a thermal disturbance or temperature command (a step change input to the control loop), will yield a response that is critically damped; i.e. in which there is minimal or no temperature overshoot or oscillations. If a low gain level is employed, the system response will be such that a much longer time will be required to achieve the desired steady state temperature value.

One critical parameter used in calculating the appropriate gain factor for the feedback controller is the mass of the body being cooled or heated. Other factors being equal, a greater mass will clearly require a larger gain factor than a smaller mass. Unfortunately, this is not an easy parameter to measure since the mass value that is needed is generally not the actual whole body mass but rather an effective thermal mass that represents a smaller mass volume of the patient. Depending on the degree of vasoconstriction/dilation, the peripheral tissue beds are isolated from the core temperature compartments of the patient, thus reducing the mass that is cooled or heated by over 50%, depending on patient morphology. The optimal gain factor may vary by over a factor of ten from large to small patients with mixed levels of vasoconstriction/dilation. If a single gain factor based on a hypothetical average patient were to be used for all patients, the resulting system response may be very poor for large patients while significantly overshooting the target temperature in small patients.

Accordingly, it would be desirable to provide a method and apparatus for quickly and easily determining a patient's effective thermal mass used to calculate a feedback control gain factor that is employed to control the rate of heat transfer during the induction and maintenance of hypothermia.

SUMMARY OF THE INVENTION

In accordance with the present invention, a method is provided for determining an effective thermal mass of a patient. The effective thermal mass is employed to determine a gain factor used in a feedback control system controlling patient temperature. The method begins by inducing hypothermia or hyperthermia in at least a selected portion of the patient with a device having a heat transfer surface. Next, power is transferred between the device and the patient. A change in temperature over time, which arises in the selected portion of the patient, is measured while performing the step of inducing hypothermia or hyperthermia. Finally, an effective thermal mass is calculated based on the measured power and the measured temperature change over time.

In accordance with one aspect of the invention, the selected portion of the patient in which hypothermia or hyperthermia is to be induced is an organ. Alternatively, the selected portion of the patient may be the whole body of the patient.

In accordance with another aspect of the invention, the device having a heat transfer surface is a catheter and hypothermia or hyperthermia is induced by introducing the catheter into a blood vessel supplying blood to the selected portion of the patient.

In accordance with yet another aspect of the invention a working fluid is circulated through the catheter and the power transferred between the catheter and the patient is measured by measuring a temperature differential between the working fluid as it enters the catheter and as it exits the catheter.

In accordance with another aspect of the invention, a computer readable medium is provided for determining an effective thermal mass of a selected portion of a patient in which hypothermia or hyperthermia is to be induced with a device having a heat transfer surface. The effective thermal mass is employed to determine a gain factor used in a feedback control system controlling patient temperature. The computer readable medium contains program instructions that, when loaded into a processor, cause the processor to store a measured value of power transferred between the device and the patient. The program instructions also cause the processor to store a measured value corresponding to a change in temperature over time, which arises in the selected portion of the patient while hypothermia or hyperthermia is being induced. Finally, the program instructions cause the processor to calculate and store an effective thermal mass based on the stored values of the measured power and the measured temperature change over time.

DETAILED DESCRIPTION OF THE INVENTION

Figure 1:
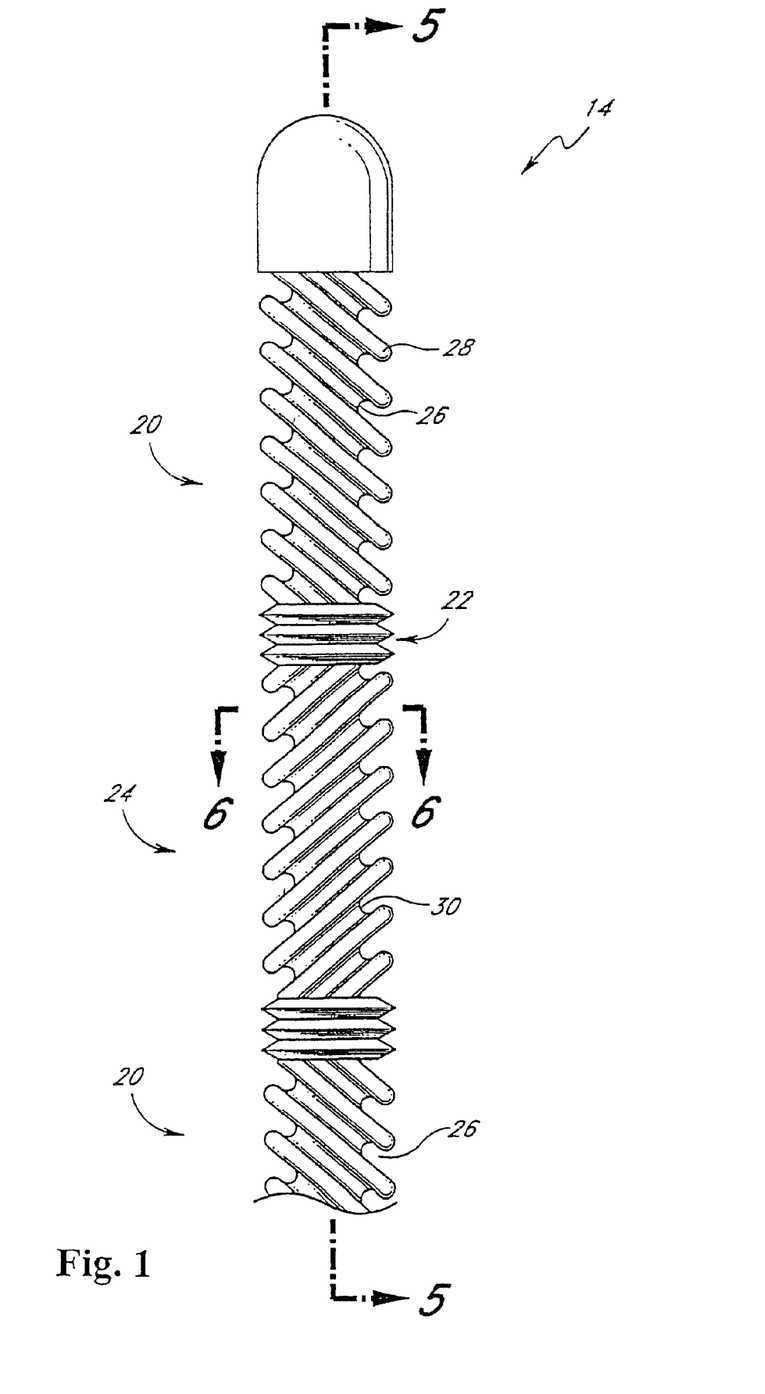
FIG. 1 is a perspective view of one embodiment of a cooling catheter according to the invention.

FIG. 1 is a perspective view of an exemplary cooling catheter that may be employed in the method of the present invention. The cooling catheter 14 is comprised of a series of articulating segments or modules. As seen in FIG. 1, a first articulating segment 20 is located at the distal end of the cooling catheter 14. A turbulence-inducing exterior surface 28 of the segment 20 is formed from one or more invaginations 26. Within the segment 20, the spiraling invaginations 26 rotate in a clockwise direction as they proceed towards the distal end of the cooling catheter 14. The segment 20 is coupled to a second segment 24 via a bellows section 22 to provide flexibility. The second segment 24 is formed from one or more spiraling invaginations 30. The spiraling invaginations 30 rotate in a counter-clockwise direction as they proceed towards the distal end of the cooling catheter 14. The segment 24 is followed by a third segment 20 having the clockwise invaginations 26. Thus, successive segments of the cooling catheter 14 alternate between having clockwise and counterclockwise invaginations. In addition, the rounded invaginations also allow the cooling catheter to maintain a relatively atraumatic profile in comparison to the use of ribs or fins, thereby minimizing the possibility of damage to the vessel wall. A cooling catheter may be comprised of 1, 2, 3 or more segments.

The exterior surface 28 of the cooling catheter 14 can be made from metal, and may comprise very high thermally conductive material such as nickel, thereby, facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The cooling catheter 14 may be manufactured by plating a thin layer of metal on a mandrel that has the appropriate pattern. In this way, the cooling catheter 14 may be manufactured inexpensively in large quantities, which is an important feature in a disposable medical device.

Figure 2:
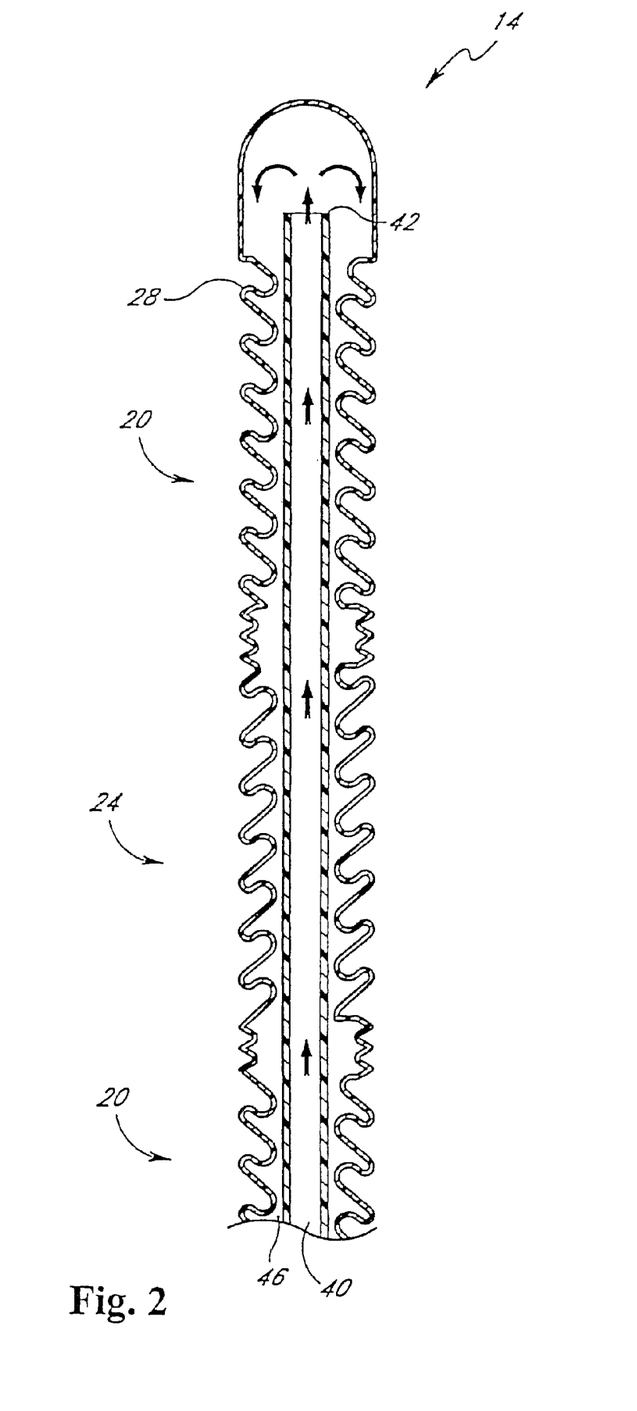
FIG. 2 is a longitudinal sectional view of the cooling catheter of FIG. 1.

FIG. 2 is longitudinal sectional view of the cooling catheter shown in FIG. 1 taken along line 5—5. Once the cooling catheter 14 is in place, a working fluid such as saline or other aqueous solution may be circulated through the cooling catheter 14. Fluid flows up a supply catheter into an insulated inner coaxial lumen 40. At the distal end of the cooling catheter 14, the working fluid exits the inner coaxial lumen 40 and enters an outer lumen 46. As the working fluid flows through the outer lumen 46, heat is transferred from the working fluid to the exterior surface 28 of the cooling catheter 14. Because the cooling catheter 14 is constructed from highly conductive material, the temperature of the external surface 28 may reach very close to the temperature of the working fluid. In order to avoid the loss of thermal energy from the working fluid within the inner coaxial lumen 40, an insulating coaxial layer 42 may be provided within the cooling catheter 14. The insulating coaxial layer 42 is comprised of a non-thermally conductive material. For example, insulation may be achieved by creating longitudinal air channels in the walls of the insulating coaxial layer 42. Alternatively, the insulating coaxial layer 42 may be constructed of a non-thermally conductive material like polytetrafluoroethylene or other polymer.

One of ordinary skill in the art will recognize that the present invention may employ devices or catheters other than those shown in FIGS. 1 and 2. For example, some catheters may include a balloon or other structure for enhancing the surface area of the portion of the catheter through which heat is transferred.

As previously mentioned, control algorithms are sometimes used to control the rate at which heat is extracted from the body by the catheter. These algorithms may be embodied in hardware, software, or a combination of both. The gain factor employed by such algorithms is dependent on the effective thermal mass of the body or organ being cooled. Thus, it is important to determine the effective thermal mass so that an appropriate gain factor can be calculated for the feedback control algorithm.

The mass of the body (organ or whole body) being cooled can be estimated by relating the power removed by the catheter to the power lost by the body.

The power removed by the catheter may be expressed as follows:

$$P_{catheter} = Mc_f \Delta T \qquad (1)$$

Where M is the mass flow rate of the fluid circulating through the catheter (typically measured in terms of cc/s), $c_f$ is the heat capacity of the fluid, and $\Delta T$ is the temperature difference between the working fluid as it enters the catheter and as it exits the catheter. Accordingly, $P_{catheter}$ can be readily calculated by measuring the mass flow of the circulating fluid and the temperature difference between the working fluid as it enters and exits the catheter.

The power removed by the catheter as determined by equation (1) may be equated to the power that is lost by the patient's body:

$$P_{catheter} = mc_b \partial T / \partial t \qquad (2)$$

Where $P_{catheter}$ is now the power lost by the patient's body and has the value calculated by equation (1), m is the effective thermal mass of the body being cooled, $c_b$ is the heat capacity of the body, and $\partial T/\partial t$ is the change in temperature per unit time of the mass being cooled.

Accordingly, the effective thermal mass of the body being cooled is:

$$m = P_{catheter}/(c_b \partial T/\partial t) \qquad (3)$$

Since all the variables in equation (3) are either known or are measurable, the effective mass can be determined.

The mass calculated in this manner is an effective thermal mass that represents the portion of the body from which power is removed (i.e., the portion of the body that is cooled). The temperature change in equation (3) represents the temperature change of the portion of the body being cooled. For example, if whole body cooling is to be performed, the change of the core body temperature may be measured to calculate mass in accordance with equation (3). In general, for whole body cooling, if the patient is vasoconstricted, the effective mass may represent about 50% of the total body mass. If the patient is vasodilated, the effective mass will be closer to the total body mass.

Alternatively, if only a selected organ such as the brain is to be cooled, then the temperature change that will be used in equation (3) would be the temperature change of the organ, assuming of course that the organ can be at least briefly considered to be largely thermally isolated from the remainder of the body. In this case the effective mass that is determined would be comparable to the mass of the organ. If the selected organ to be cooled is the brain, for example, the catheter is placed in the common carotid artery, the internal carotid artery, or both. The temperature changed used in equation (3) will be measured by inserting a temperature sensor into the brain or via a tympanic membrane sensor, both of which are commercially available.

EXAMPLE

In an animal study, whole body cooling was accomplished by inserting the catheter through the femoral vein and then through the inferior vena cava as far as the right atrium and the superior vena cava. Cooling was initiated by circulating a working fluid at a flow rate of 5 cc/sec. The temperature differential between the fluid entering the catheter and the fluid exiting the catheter was 17° C. Accordingly, the power extracted by the catheter was 354 watts.

The body core temperature was measured through the esophagus. Twenty minutes after cooling was initiated, the rate at which the core temperature changed was measured over a period of about ten minutes, resulting in an average temperature change of about 4° C./hr.

From equation (3) above, the effective thermal mass is:

$$m = 354 \text{ watts}/(0.965 \text{ watts/kg C.}°)(10°\text{c./hr}) = 37 \text{ kg}$$

The total mass of the animal was 53 kg, and thus the effective mass was found to be 69% of the total mass.

Although various embodiments are specifically illustrated and described herein, it will be appreciated that modifications and variations of the present invention are covered by the above teachings and are within the purview of the appended claims without departing from the spirit and intended scope of the invention. For example, while the cooling catheter has been described as a device that employs a circulating fluid, other types of catheters may alternatively be employed. For example, the catheter may employ a compressed refrigerant that is pumped through the catheter into an expansion element.

What is claimed is:

1. A method for determining an effective thermal mass of a patient, said method comprising the steps of:
    inducing hypothermia or hyperthermia in at least a selected portion of the patient;
    measuring a parameter characteristic of power transferred to or from the patient while performing the step of inducing hypothermia or hyperthermia; and
    calculating an effective thermal mass based at least in part on the measured parameter.

2. The method of claim 1 further comprising the step of measuring a change in temperature of the patient while performing the step of inducing hypothermia or hyperthermia, and wherein the step of calculating the effective thermal mass includes the step of calculating the effective thermal mass based at least in part on the measured parameter and the measured temperature.

3. The method of claim 2 wherein said temperature of the patient is the whole body core temperature of the patient.

4. The method of claim 1 wherein the step of inducing hypothermia or hyperthermia includes the step of introducing a catheter into a blood vessel to transfer heat between the patient and the catheter.

5. The method of claim 4 further comprising the step of circulating a working fluid through the catheter.

6. The method of claim 5 wherein the step of measuring a parameter characteristic of the power transferred between the catheter and the patient includes the step of measuring a temperature differential between the working fluid as it enters the catheter and as it exits the catheter.

7. The method of claim 6 wherein the step of measuring a parameter characteristic of the power transferred between the catheter and the patient further includes the step of measuring the power based on the measured temperature differential and a mass flow rate of the working fluid circulating through the catheter.

8. The method of claim 4 wherein the selected portion of the patient is the brain and the catheter is introduced into the carotid artery.

9. The method of claim 4 wherein the selected portion of the patient is the whole body and the catheter is introduced into the inferior vena cava.

10. The method of claim 5 wherein the feedback control system determines the temperature of the working fluid as it enters the catheter.

11. A method for controlling the temperature of at least a selected portion of a patient, said method comprising the steps of:
    introducing a catheter into a blood vessel supplying blood to the selected portion of the patient;
    heating or cooling the catheter to introduce or remove heat from the selected portion of the patient, said heating or cooling being performed at a rate determined by a feedback control algorithm that employs a feedback control gain factor; and
    wherein the step of heating or cooling includes the step of calculating an effective thermal mass for determining the feedback control gain factor, said calculating step including the steps of:
    measuring a parameter characteristic of power transferred between the catheter and the patient; and
    calculating the effective thermal mass based at least in part on the measured parameter.

12. The method of claim 11 further comprising the step measuring a change in temperature which arises in the selected portion of the patient while heating or cooling the catheter, and wherein the step of calculating the effective thermal mass includes the step of calculating the effective thermal mass based at least in part on the measured parameter and the measured temperature.

13. The method of claim 11 wherein said selected portion of the patient is an organ.

14. The method of claim 11 wherein said selected portion of the patient is the whole body of the patient.

15. The method of claim 11 wherein the heating or cooling step includes the step of circulating a working fluid through the catheter.

16. The method of claim 15 wherein the step of measuring a parameter characteristic of the power transferred between the catheter and the patient includes the step of measuring a temperature differential between the working fluid as it enters the catheter and as it exits the catheter.

17. The method of step 16 wherein the step of measuring a parameter characteristic of the power transferred between the catheter and the patient further includes the step of measuring the power based on the measured temperature differential and a mass flow rate of the working fluid circulating through the catheter.

18. The method of claim 15 wherein the feedback control algorithm determines the temperature of the working fluid as it enters the catheter.

19. The method of claim 15 wherein the feedback control algorithm determines a mass flow rate of the working fluid circulating through the catheter.

20. The method of step 11 wherein the selected portion of the patient is the brain and the catheter is introduced into the carotid artery.

21. The method of claim 11 wherein the feedback control algorithm employs a PID controller.

22. A computer readable medium for determining an effective thermal mass of a selected portion of a patient in which hypothermia or hyperthermia is to be induced with a device having a heat transfer surface, said effective thermal mass being employed to determine a gain factor used in a feedback control system controlling patient temperature, said computer readable medium containing program instructions that, when loaded into a processor, cause the processor to perform the steps of:
    storing a measured value of a parameter characteristic of power transferred between the device and the patient; and
    calculating and storing an effective thermal mass based at least in part on the stored value of the measured parameter.

23. The medium of claim 22 further comprising the step of storing a measured value corresponding to a change in temperature which arises in the selected portion of the patient while hypothermia or hyperthermia is being induced and wherein the step of calculating and storing an effective thermal mass includes the step of calculating and storing an effective thermal mass based at least in part on the stored values of the measured parameter and the measured temperature.

24. The medium of claim 22 wherein said selected portion of the patient is an organ.

25. The medium of claim 22 wherein said selected portion of the patient is the whole body of the patient.

26. The medium of claim 22 wherein said device having a heat transfer surface is a catheter introduced into a blood vessel supplying blood to the selected portion of the patient.

27. The medium of claim 26 wherein the step of storing a measured value of a parameter characteristic of the power transferred between the catheter and the patient includes the step of storing a measured value of a temperature differential between a working fluid as it enters the catheter and as it exits the catheter.

28. The medium of claim 27 wherein the step of storing a measured value of a parameter characteristic of the power transferred between the catheter and the patient further includes the step of storing a measured value of the power based on the measured value of the temperature differential and a mass flow rate of the working fluid circulating through the catheter.

29. The medium of claim 22 wherein the feedback control system employs a PID controller.

* * * * *